US007686833B1

(12) United States Patent
Muhanna et al.

(10) Patent No.: US 7,686,833 B1
(45) Date of Patent: Mar. 30, 2010

(54) BALL JOINTED PEDICLE SCREW AND ROD SYSTEM

(76) Inventors: Nabil L. Muhanna, 2128 Valley Rd., Gainesville, GA (US) 30501; David L. Schalliol, 4611 Circle Dr., Oakwood, GA (US) 30566

( * ) Notice: Subject to any disclaimer, the term of this patent is extended or adjusted under 35 U.S.C. 154(b) by 78 days.

(21) Appl. No.: 10/817,125

(22) Filed: Apr. 2, 2004

(51) Int. Cl.
*A61B 17/70* (2006.01)

(52) U.S. Cl. ................... 606/257; 606/272

(58) Field of Classification Search .......... 606/60, 606/61, 72, 73, 86, 87, 250–262, 278–279, 606/300–301, 309, 314–315, 266–267; 403/122–144
See application file for complete search history.

(56) References Cited

U.S. PATENT DOCUMENTS

| | | | | |
|---|---|---|---|---|
| 1,086,145 | A * | 2/1914 | Dodds | 411/379 |
| 1,877,332 | A * | 9/1932 | Laisne | 280/93.511 |
| 3,530,548 | A * | 9/1970 | Gearin | 403/300 |
| 4,473,240 | A * | 9/1984 | Sanada | 280/771 |
| 5,385,583 | A * | 1/1995 | Cotrel | 606/270 |
| 5,437,669 | A * | 8/1995 | Yuan et al. | 606/61 |
| 5,536,268 | A * | 7/1996 | Griss | 606/61 |
| 5,540,688 | A * | 7/1996 | Navas | 606/61 |
| 5,885,286 | A | 3/1999 | Sherman | |
| 5,910,142 | A * | 6/1999 | Tatar | 606/61 |
| 5,984,923 | A * | 11/1999 | Breard | 606/61 |
| 6,077,262 | A * | 6/2000 | Schlapfer et al. | 606/305 |
| 6,187,005 | B1 * | 2/2001 | Brace et al. | 606/61 |
| 6,368,321 | B1 * | 4/2002 | Jackson | 606/61 |
| 6,471,705 | B1 | 10/2002 | Biedermann | |
| 6,554,832 | B2 * | 4/2003 | Shluzas | 606/61 |
| 6,565,567 | B1 | 5/2003 | Haider | |
| 6,726,392 | B2 * | 4/2004 | El-Haw et al. | 403/56 |
| 6,802,844 | B2 * | 10/2004 | Ferree | 606/61 |
| 6,835,196 | B2 * | 12/2004 | Biedermann et al. | 606/61 |
| 6,896,677 | B1 * | 5/2005 | Lin | 606/266 |
| 2005/0070899 | A1 * | 3/2005 | Doubler et al. | 606/61 |
| 2005/0171538 | A1 * | 8/2005 | Sgier et al. | 606/61 |
| 2005/0216001 | A1 * | 9/2005 | David | 606/61 |

* cited by examiner

*Primary Examiner*—Thomas C Barrett
*Assistant Examiner*—James L. Swiger
(74) *Attorney, Agent, or Firm*—Womble Carlyle Sandridge & Rice, PLLC (57) ABSTRACT

A pedicle screw assembly includes pedicle screw having a plurality of spaced-apart posts. A ball collet having a ball collet bore is seated on the pedicle screw between the posts and a rod is gripped by an inner surface of the ball collet bore. The assembly also includes a cap that is coupled to the posts, the cap applying a compressive force to the ball collet against a seat of said pedicle screw. A free end of the rod may be provided with various structures to enable such free end to be retained by another pedicle screw.

30 Claims, 9 Drawing Sheets

BALL JOINTED PEDICLE SCREW AND ROD SYSTEM

FIELD OF THE INVENTION

The present invention is related to screws, such as those used in orthopedic surgery, and associated rods connecting such screws.

BACKGROUND

After a patient undergoes lumbar spinal disc surgery, there is a need to install pedicle screws and stabilizing rods to support the vertebrae during the fusion process that takes place in the weeks after surgery. Pedicle screws are inserted into the vertebrae in positions or axes that are typically not in a straight line. Part of the reason for this misalignment is natural anatomy of the spine, and part is the inability to accurately place screws where they would ideally be placed because of adjacent tissue, weak points in the vertebrae structure, and also because screws may not always be placed evenly in several levels. To compensate for this misalignment, the screws have to be jointed, the heads must swivel and rotate, attachments have to be installed, and invariably the rods themselves have to be bent in a 3-dimensional space to fit the contour through this maze of misaligned screw heads and conforming rod clamps. These multiaxial screws and clamps are an attempt by pedicle screw manufacturers to help make a best-fit path for the rod, but they are cumbersome to install, unstable, and expensive. To make matters worse, the rods still sometimes have to be bent. Rod bending is a process that takes a good eye by the surgeon. Sometimes, the surgeon will have to make a template out of wire or soft tubing, and then go to the bench and try to form the rod with hand tools to fit the misaligned 3 dimensional contour. This is pretty much a trial and error process. This could be very frustrating and time consuming, and the entire surgical staff is held up until there is an acceptable fit of the rod to the screws.

SUMMARY OF THE INVENTION

In one aspect, the present invention is directed to a pedicle screw assembly including a pedicle screw having a plurality of spaced-apart posts. A ball collet having a ball collet bore is seated on the pedicle screw between the posts and a rod is gripped by an inner surface of the ball collet bore. The assembly also includes a cap that is coupled to the posts, the cap applying a compressive force to the ball collet against a seat of said pedicle screw.

In another aspect, the present invention is direction to a pedicle screw assembly that includes a pedicle screw having a longitudinal axis and a pair of spaced-apart threaded posts extending therealong. The threaded posts define a channel therebetween. The assembly also includes a ball collet having a bore formed therein, a rod member having an end that is insertable into the bore of the ball collet, and a threaded cap. The assembly is adjustable between disassembled state in which the pedicle screw, ball collet, rod and cap are not secured to one another, and an assembled state in which the ball collet is seated in the channel, the rod is gripped by an inner surface of the ball collet bore, and the cap is screw-coupled to the post.

In still another aspect, the present invention is directed to a pedicle screw assembly comprising first and second pedicle screws. Each pedicle screw has a longitudinal axis and a pair of spaced-apart threaded posts extending therealong, each pair of threaded posts defining a channel therebetween. The assembly also includes a ball collet having a bore formed therein, a rod member having a first end that is insertable into the bore of the ball collet and a bulbous second end, and a pair of threaded caps. The assembly is adjustable between a disassembled state in which the first and second pedicle screws, ball collet, rod and caps are separated from one another, and an assembled state in which the ball collet is seated in the channel of the first pedicle screw, the rod is gripped by an inner surface of the ball collet bore, the bulbous second end of the rod occupies the channel of the second pedicle screw, and the first and second caps are screw-coupled to the threaded posts of respective first and second pedicle screws.

In yet another aspect, the present invention is directed to a pedicle screw assembly comprising first, second and third pedicle screws. Each pedicle screw has a longitudinal axis and a pair of spaced-apart threaded posts extending thereal-ong, each pair of threaded posts defining a channel therebetween. The assembly also includes a pair of ball collets, each provided with bore therethrough, a pair of rods, and three threaded caps to mate with the pairs of posts. A first rod has a first end insertable into the ball collet bore of the first ball collet, and a second end provided with a first partial hemispherical ball member, the first partial hemispherical ball member having a convex surface facing an inboard side of the second end, and a centrally located protrusion facing an outboard side of the second end. A second rod has a first end insertable into the ball collet bore of the second ball collet, and a second end provided with a second partial hemispherical ball member, the second partial hemispherical ball member having a convex surface facing an inboard side of the second end, and a centrally located recess facing an outboard side of the second end. The assembly is adjustable between a disassembled state in which these components are not secured to one another, and an assembled state in which the first and second ball collets occupy channels of the first and second pedicle screws, respectively, the first rod is gripped by an inner surface of the first ball collet bore and the second rod is gripped by an inner surface of the second ball collet bore, the first and second partial hemispherical ball members oppose one another within the channel of the third pedicle screw with the centrally located protrusion at least partially entering the recess, and the caps are screw-coupled to the pairs of threaded posts. The outboard sides of the second ends of both rods may be provided with a conical surface.

In yet another aspect, the present invention is directed to one-piece pedicle screw formed from titanium or an alloy thereof, the one-piece pedicle screw comprising a threaded insertion portion aligned with said longitudinal axis, a top of the threaded insertion portion connected to a yoke portion comprising a pair of spaced apart posts, said posts having arcuate cross-sections and defining a substantially cylindrical channel, end portions of the posts having radially inwardly facing threads, a base of the channel being provided with a concave seat having a spherical contour. The one-pedicle screw may have a ball collet seated in the concave seat.

In yet another aspect, the present invention is directed to an orthopedic ball collet comprising a generally spherical body formed from titanium or an alloy thereof, the body having a ball collet bore formed therethrough along a body axis, the body being provided with a plurality of slots spaced about a periphery thereof, each slot extending in an axial direction along the body axis and connecting an outer surface of the ball collet with the ball collet bore, each slot communicating with a single end of the ball collet bore and alternating slots communicating with opposite ends of the ball collet bore. The ball collect may be split into two mating portion. Each mating portion preferably has a resilient tongue provided with a convex inner surface configured to abut a complementary surface on the other mating portion.

In yet another aspect, the present invention is directed to a method of securing a rod in an orthopedic procedure. The method comprises seating a compressible hollow object in a screw having threaded posts, inserting the rod into the compressible hollow object, and applying and tightening a cap to the threaded posts, thereby causing the hollow object to at least partially deform and grip the rod.

In yet another aspect, the present invention is directed to kits comprising two or more of the individual components.

BRIEF DESCRIPTION OF THE DRAWINGS

The present invention is now described with respect to the embodiments seen in following drawings, in which.

DETAILED DESCRIPTION OF THE INVENTION

Figure 1:
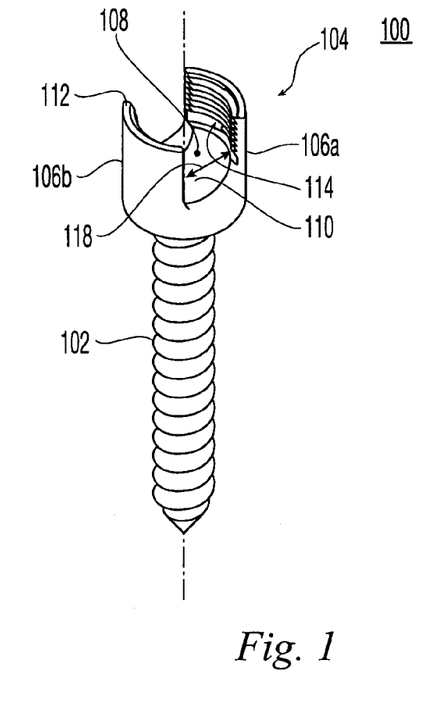
FIG. 1 shows a pedicle screw in accordance with the present invention

FIG. 1 shows a pedicle screw 100 in accordance with present invention. Pedicle screw 100 has a longitudinal axis along which a threaded insertion portion 102 is aligned. The top of the threaded insertion portion is connected to a yoke portion 104. Yoke portion 104 comprises a plurality of spaced apart threaded posts 106a, 106b separated by a circumferential gap 118 and defining a substantially cylindrical channel 108 therebetween. At the base of the channel 108, the pedicle screw 100 is provided with a concave seat 110 having a spherical contour. The posts 106a, 106b extend in a direction away from the threaded insertion portion 102, the end portions of the ports terminating in radially inwardly facing threads 112 formed on the posts' inner surfaces 114. Pedicle screw 100 preferably is formed of titanium, or an alloy thereof.

Preferably, the threaded insertion portion 102 and the yoke portion 104 have unitary construction, being formed from a single piece of metal, and so the yoke portion 104 does not swivel relative to the insertion portion, making for a one-piece pedicle screw.

Figure 2A:
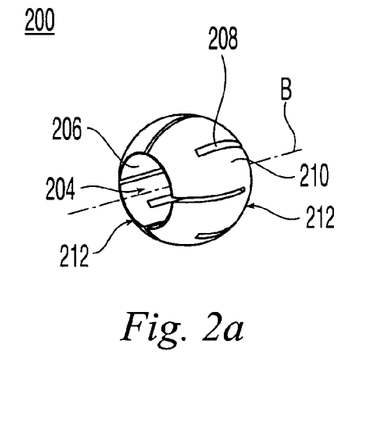
FIGS. 2a & 2b show a perspective view and a side view, respectively, of a ball collet in accordance with the present invention.
Figure 2B:
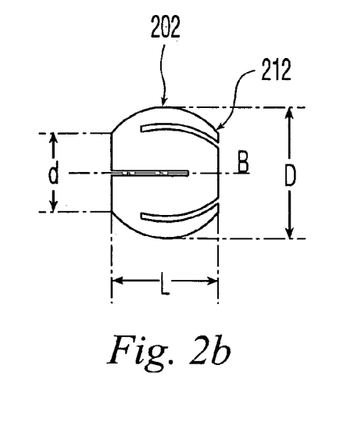

As seen in FIGS. 2a and 2b, a ball collet 200 in accordance with the present invention has a generally spherical body 202 and a ball collet bore 204 extending through the body along a body axis B. The inner surface 206, or wall, of the bore 204 has a cylindrical shape. A plurality of axially directed slots 208 are formed through a thickness of the ball collet. As seen in FIG. 2a, the slots 208 connect the spherical outer surface 210 of the ball collet with the inner surface 206 of the bore 204, each slot communicating with one end 212 of the ball collet. In a preferred embodiment a total of 8 circumferentially evenly spaced slots are provided, alternating slots communicating with opposite ends of the bore 204.

The ball collet 200 preferably is machined from a solid spherical ball which preferably is formed of titanium, or an alloy thereof. The machining may be done using various metal-cutting tools, such as milling cutters, boring tools, and the like. Alternatively, a CNC wire-type EDM machine to make all the needed cuts.

The solid spherical ball has an outer diameter D of preferably 0.375". A ball collet bore 204 of diameter d is then made along the body axis B. Preferably, the bore diameter d is slightly larger than 5.5 mm, which is the diameter of a standard-size surgical-grade rod material. It is noted, however, that other diameters for both D and d may be used, and that a range of d/D ratios may be used, as well. Forming the bore 204 results in a foreshortening of the ball collet to have an axial length L measured along the body axis B. From geometric principles, it can be seen that the axial length L depends on the ball diameter D and the bore diameter d. The axial slots 208 of length l are then made, l preferably being between 75-95% of axial length L.

Figure 2C:
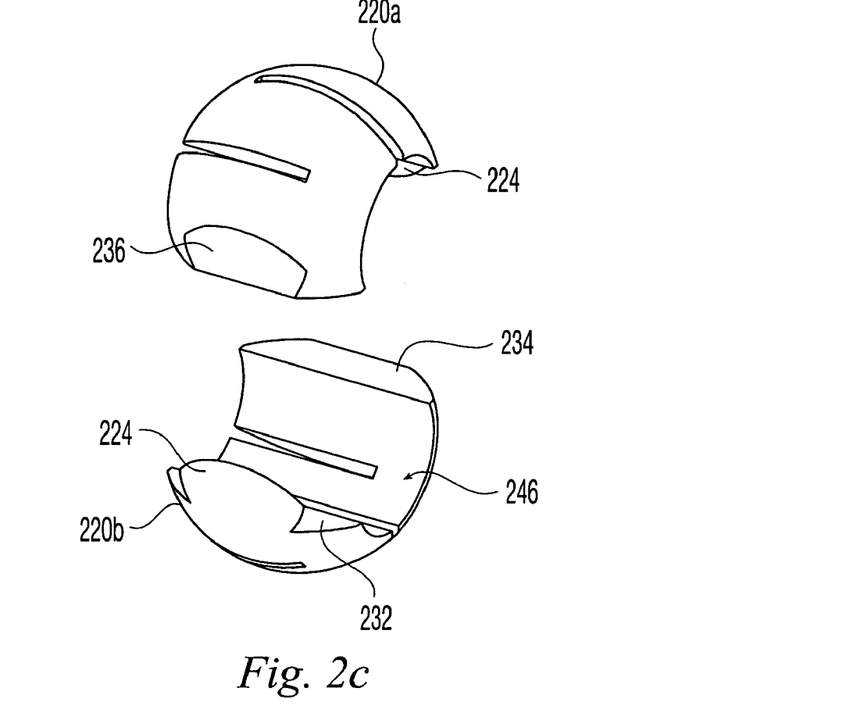
FIGS. 2c & 2d shows a perspective exploded view, and an assembled end-view, respectively, of a split-ball ball collet in accordance with the present invention.
Figure 2D:
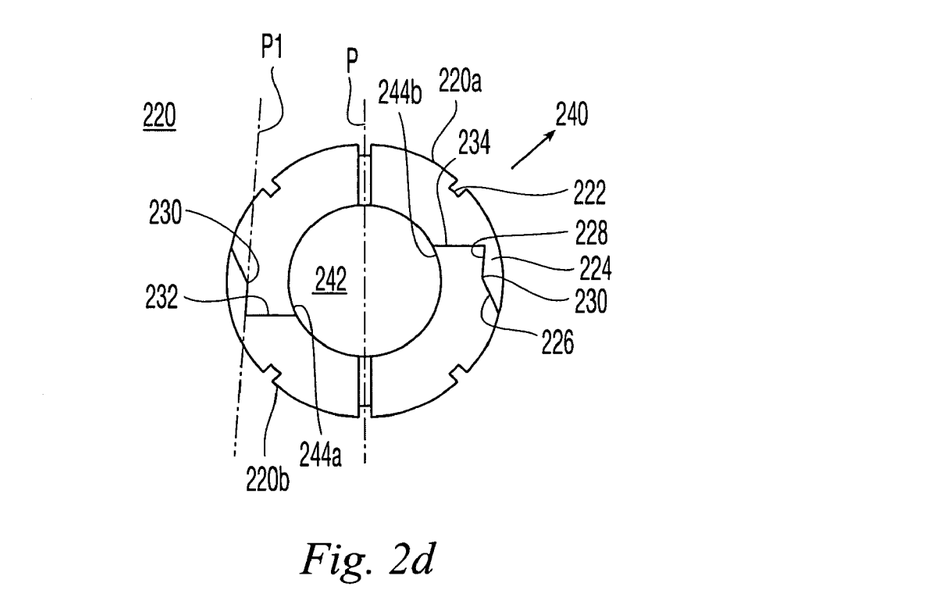

As seen in FIGS. 2c and 2d, it may be possible to provide a split-ball ball collet 220 comprising two identical, mating portions 220a, 220b. The split-ball ball collet 220 differs from the ball collet 200 in two principal regards: first, it is split into two portions; and second, it has no slots 222 on diametrically opposing portions where it is split.

Such a device may be used when, for whatever reason, it is not possible to place a ball over the end of a rod. This may happen, for instance, when a stabilizing rod has previously been installed and it is desired to replace a screw, or insert another screw, along a mid-section of the rod.

Each portion 220a, 220b has a resilient tongue 224 whose outer surface substantially conforms to the spherical exterior of the ball. The tongue 224 has a convex inner surface which, in a preferred embodiment, comprises two planar component surfaces 226, 228. As seen in FIG. 2d, the first planar component surface 226 is sloped inwardly from the spherical exterior towards an interior portion of the ball collet 220, and connects to the second planar component surface 228 at an interior line represented by apex 230. The tongue's second planar component surface 228 lies in a plane P1 which is oblique relative to a bisector plane P of the ball collet 220. Second component surface 228 therefore angles away from the bisector plane from the interior line.

The second component surface of one portion 220a, 220b ends at a step 232 which, in the assembled state opposes a complementary step 234 formed on the other portion 220b, 220a. While steps 232, 234 are shown as straight lines that are parallel to a diameter of the ball collet 220, it is understood that they may instead be sloped, curved or even take on a V-shape, so long as one is complementary to the other. Furthermore, when ball collet 200 is assembled, the first planar component surface 226 of one portion 220, 220b abuts the exposed surface 236 of the complementary portion 220b, 220a, respectively.

From FIG. 2d, it is evident that the two portions, though in abutment with one another, can easily be separated; nothing prevents portion from 220a from being removed upon application of a force in a direction represented by arrow 240. However, this is not case once a rod is positioned in the bore 242. During assembly, a rod is placed in the cradle 246 provide by portion 220b, and portion 220a is placed over the rod, one or both of the tongues 224 bending slightly outward as their convex surfaces fit over step 234 on the complementary portion. Thus, the tongues help the upper portion 220b 'snap' into place. Once assembled with a rod in place, the lower, inner edge 244 of portion 220a, the upper, inner edge 244b of portion 220b, and the convex tongues cooperate to resist removal of portion 220a when a rod is positioned in the bore 242.

While in a preferred embodiment, the tongue's inner surface comprises two planar component surfaces 226, 228, this is not an absolute requirement. For instance, the tongue may be a continuously curving surface having a convex section. Alternatively, the tongue may have one planar surface and another that is curved. The important characteristic is that the inner surface of the tongue have a convex contour that helps resist separation from the complementary portion when a rod is positioned in the bore 242.

Figure 3A:
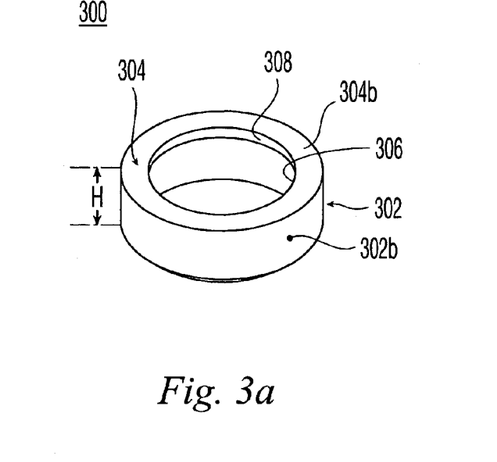
FIGS. 3a & 3b show a perspective view from above and below, respectively, of a crown in accordance with the present invention.
Figure 3B:
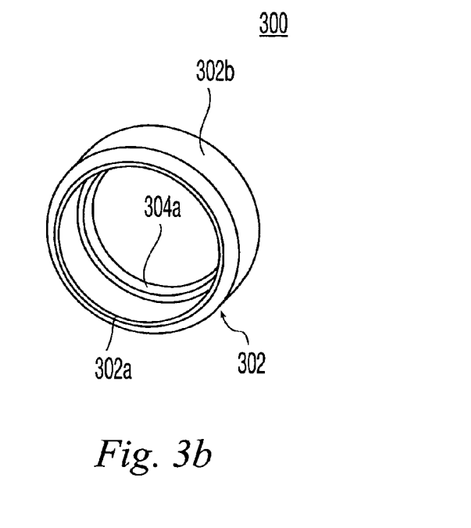

As seen in FIGS. 3a and 3b, a crown 300 in accordance with the present invention comprises a cylindrical skirt 302 having a crown height H, an inner surface 302a and an outer surface 302b. Connected at a top end of its skirt 302, is a radially inwardly projecting flange 304 having an inner surface 304a and an outer surface 304b. The radially innermost portion of the flange 304 terminates in a rim 306 having threads 308. Crown 300 preferably is formed from titanium, or an alloy thereof.

Figure 4A:
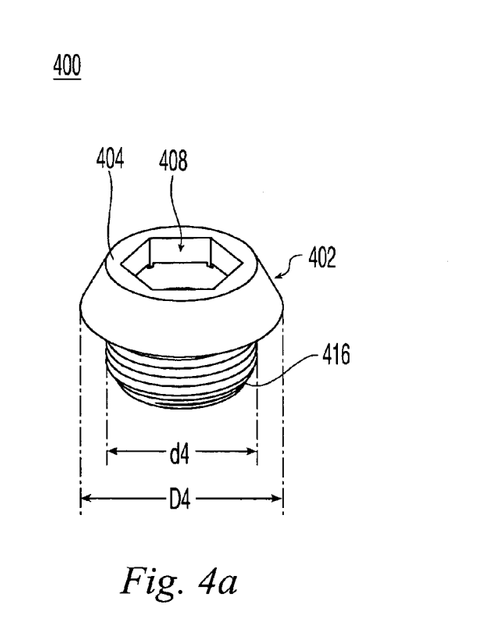
FIGS. 4a & 4b show a perspective view from above and below, respectively, of a clamping screw in accordance with the present invention.
Figure 4B:
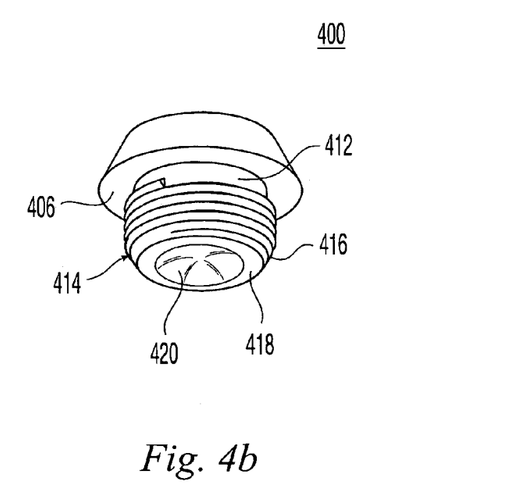

As seen in FIGS. 4a and 4b, a threaded clamping screw 400 in accordance with the present invention has a head portion 402 comprising a disk-like upper surface 404 and a disk-like lower surface 406. The head portion itself is preferably beveled at a 30° angle, as seen in FIGS. 4a and 4b. The upper surface 404 is provided with a socket 408 configured to receive an "Allen-type" hex-wrench, or the like, for screwing and unscrewing the clamping screw. The head portion 402 is connected, via a narrow neck portion 412, to a threaded base portion 414, a diameter D4 of the head portion 402 being larger than a diameter d4 of the threaded base portion 414.

The threaded base portion 414 is provided with radially outwardly facing threads 416 configured and dimensioned to mate in a screw-coupled manner with the radially inwardly facing threads 112 belonging to the posts 106a, 106b of the pedicle screw 100, and also with the threads 308 formed on the rim of the radially innermost portion of the flange 304. A lower surface 418 of clamping screw 400 is provided with a concave lower contacting surface 420 having a spherical contour having a contour diameter similar to the diameter D of the ball collet. Clamping screw 400 preferably is formed from titanium, or an alloy thereof.

Figure 5A:
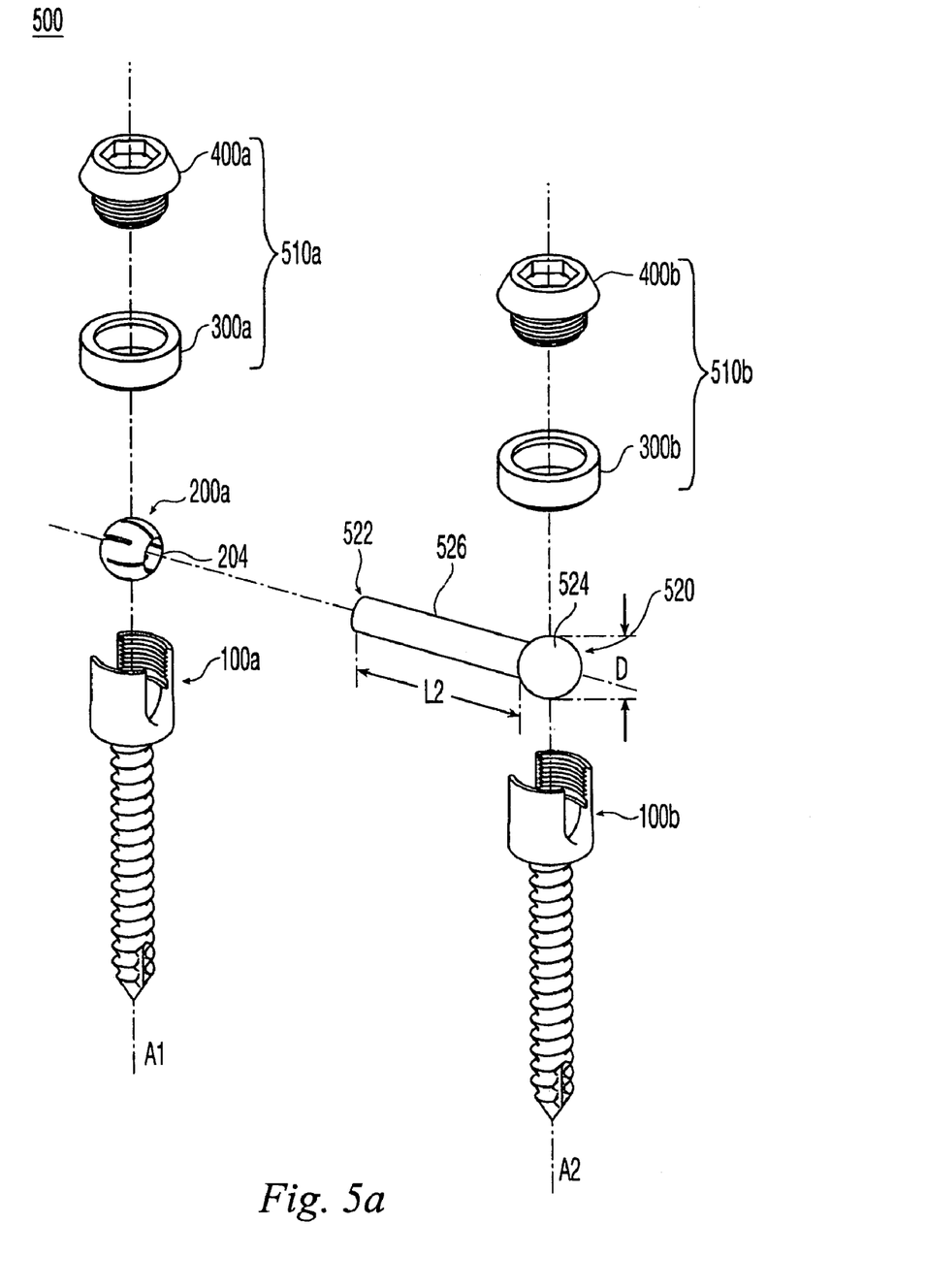
FIGS. 5a and 5b show an exploded view and an assembled view of a two-screw assembly in accordance with the present invention.

FIG. 5a shows an exploded view of a pedicle screw assembly 500 comprising two a pedicle screws 100a, 100b of the sort described above, having respective longitudinal axes A1, A2. The assembly also includes a ball collet 200a, a ball rod 520 and two threaded caps 510a, 510b, each cap comprising a crown 300a, 300b, respectively, and clamping screws 400a, 440b, respectively, of the sort described above.

Ball rod 520 has a first end 522, and bulbous second end 524 and a shaft 526 between the two ends. The bulbous second end 522 comprises a spherical ball member having unitary construction with the remainder of the ball rod. A diameter D of the spherical ball member is similar to a diameter D of the ball collet. The ball rod length L2 may vary from ball rod to ball rod, and typically comes in a predetermined variety of standard sizes.

Assembly of the pedicle screw assembly 500 is next discussed.

The cap 510a is first pre-assembled by having the threads 416 of the clamping screw 400a first engage the threads 308 of the crown 300a, and then travel past them so that the crown is loosely retained by the clamping screw, the crown's rim 306 being between the clamping screw's threads 416 and the lower surface 406 of the clamping screw's head 402. With the ball collet 200a placed in the seat 110 of pedicle screw 100a, the cap 510a is then placed atop the posts 106a, 106 with the crown's skirt 302 at least partially encircling the posts 106a, 106b, the lower surface 304a of the flange 304 overlying the posts 106, 106b, and the threads 416 of the clamping screw 400a abutting the topmost portion of the posts 106a, 106b.

As an alternative to pre-assembling the cap 510a, with the ball collet 200a in the seat 100, the crown 300a is first placed atop the posts 106a, 106b by itself, and then the threaded base portion 414 of the clamping screw 400a is brought into abutment with the crown's rim 306. The clamping screw 400a is then initially screwed into the threads 308 of the crown 300a so that the two-piece cap 510a is formed in place.

Regardless of exactly how the cap 510a is formed, the clamping screw 400a is further rotated, such that the threads 416 of the clamping screw 400 begin to engage threads 114 of the pedicle screw posts 106a, 106b. As the clamping screw 400a is further rotated, it may push against the threaded posts 106a, 106b in a radially outward direction, the skirt 302 of the crown 300 helping confine excessive radially outward bulging of the posts 106a, 106b.

Prior to inserting the first end 522 of the rod 520 into the ball collet bore 204, the ball collet 200a may need to be rotated in the seat 110 until its ball collet bore 204a is aligned with the circumferential gap 118 between the posts 106a, 106b. The first end 522 of the ball rod 520 is then inserted into the bore 204a such that at least a portion of the rod shaft 526 is surrounded by inner surfaces 206 of the ball collet bore 204.

The clamping screw 400a is further rotated so that the concave lower surface 420 of the clamping screw 400a is penetrated by, and abuts, the spherical outer surface 210 of the ball collet. The ball collet is thus trapped between the spherical contour of the concave lower surface 420 belonging to the clamping screw 400a of the cap 510a and spherical contour of the concave seat 110 of the pedicle screw 100a on which the ball collet 200a is seated.

Upon further rotation, the clamping screw 400a first begins to press the ball collet 200a against the concave seat 110, along the longitudinal axis A1, and then begins to deform the ball collet 200a, narrowing its extent along the longitudinal axis A1 and causing it bulge in a lateral direction transverse to the longitudinal axis A1. As the ball collet is deformed, inner surfaces 206 of the ball collet bore 204 grip the shaft 526, preventing removal of the rod, upon application of an axially applied push-out force of up to 250 lbs., and more preferably, up to 300 lbs. The torque applied is sufficient for the rim of the ball collet bore 204 to indent the shaft 526 of the rod 520, leaving a permanent mark thereon. Preferably, the clamping screw is tightened to at least 120 inch-pounds of torque, and more preferably to 140 inch-pounds.

Figure 5B:
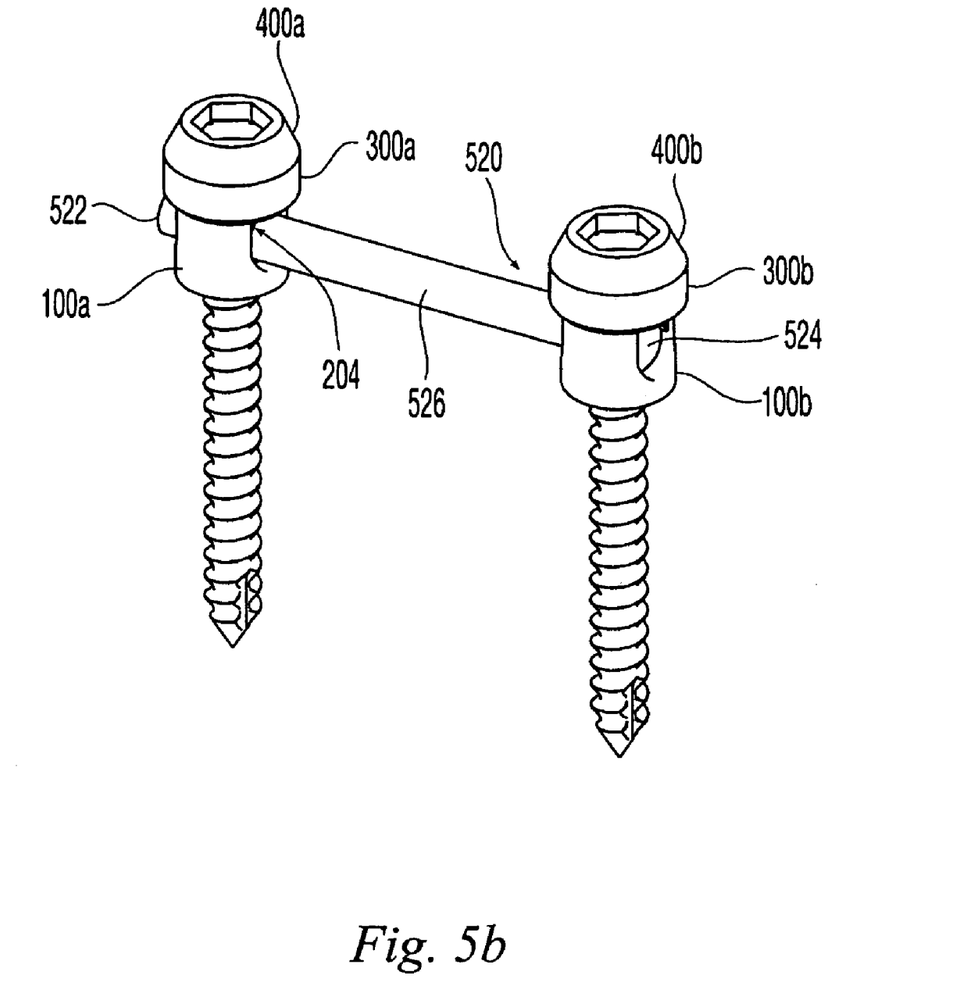

The foregoing steps result in the formation of an assembly comprising the pedicle screw, the ball collet, the ball rod and the cap, with the ball collet occupying the channel and gripping the ball rod. The second pedicle screw 100b may now be added to this assembly. For this, the bulbous second end 524 of the ball rod 520 is positioned in the channel 108 of the second pedicle screw 100b, and the cap 510b is screw-coupled to the pedicle screw 100b, as described above, thereby forming a two-screw assembly. During this process, the bulbous second end 524 of the ball rod 520 first becomes trapped between the cap 510b and the seat 110 of the second pedicle screw 100b. Then, as the cap 510b is further screwed on, the bulbous second end 524, is held sufficiently tightly between the cap and the seat so as resist rotational movement within the channel, at torques of up to 100 inch-pounds and more preferably up to 125 inch-pounds.

During a surgery connecting a two vertebrae (i.e., a "one-level" surgery), two such assemblies 500, one on the left side of the vertebral column, and another on the right side of the column are typically used. Generally speaking, two holes are drilled on each side of the vertebral column, and the pedicle screws are inserted into the holes such that the gaps 118 of the inserted screws on one side of the column more or less face in the same direction, as do the gaps 118 of the inserted screws on the other side of the column. Similar steps are then taken on each side of the column, and so only the steps on one side are described next.

The bulbous second end 524 of the ball rod shaft 526 is first positioned in the channel 108 of the second pedicle screw 100b. Next, the ball collet 200a is mounted onto the ball rod shaft 526 as the ball collet bore 204 is brought over the ball rod's first end 522. Then the ball collet 200a, while still on the ball rod shaft 526, is then slipped between the posts and into the channel 108 of the first pedicle screw 100a, it being understood that the ball collet 200a may travel slightly along the ball rod shaft 526 as it is brought into the channel. Alternatively, the ball collet 200a made be introduced into the channel of the first pedicle screw 100a first, the first end of the rod 520 inserted into the ball collet bore 204 next, and then the bulbous second end 524 of the ball rod introduced into the channel of the second pedicle screw 100b. As yet another set of alternatives, the ball collet is mounted onto the ball rod shaft 524 first, and then either (a) the ball collet is introduced into the channel of the first pedicle screw 100a first, and then the bulbous second end of the ball rod is introduced into the channel of the second pedicle screw 100b, or (b) the bulbous second end of the ball rod is introduced into the channel of the second pedicle screw 100b first, and then the ball collet is introduced into the channel of the first pedicle screw, or (c) the ball collet and the bulbous end of the ball rod 520 are introduced into the channels of respective first and second pedicle screws simultaneously.

Regardless of which of these alternatives is used, the result is an assembly comprising two spaced apart pedicle screws, one having the bulbous end of a ball rod in its channel and the other having a ball collet 200a in its channel with the shaft 524 of the rod 520 positioned in the ball collet bore 204. The caps 510a, 510b may then be applied in the manner described above, perhaps by alternatingly incrementally tightening them first, then finally tightening the cap 510 of the second pedicle screw 100b in which the bulbous second end 524 is seated, and only then finally tightening the cap 510a of the first pedicle screw 100a which accommodates the ball collet 200a in whose bore 204 the rod is gripped.

When the two-screw assembly 500 is in the assembled state, there is no requirement that the pedicle screws 100a, 100b be at the same vertical position relative to one another, or, for that matter, be oriented such that their longitudinal axes A1, A2 are perfectly parallel to one another. This is made possible by the free play afforded the rod shaft 526 by virtue of the rotatability of the ball rod 520 within the channel 108 of the second pedicle screw 100b, prior to finally tightening the caps 510a, 510b. This feature allows one-piece pedicle screws in which the insertion portion and the yoke portion are formed with unitary construction to be used in a two-level surgery. As mentioned above, ball rods come in different lengths. During surgery, rods of differing lengths are made available, a rod of an appropriate length perhaps being selected during the surgery itself. It is further understood that the various components are packaged, sold or otherwise made available as kits since they are to be used together. Thus, a first kit may comprise a pedicle screw, crown and clamping screw; a second kit may comprise a pedicle screw, ball collet, crown and clamping screw; a third kit may comprise a pedicle screw, ball rod, crown and clamping screw; a fourth kit may comprise two pedicle screws, two crowns and two clamping screws; a fifth kit may comprise all the items of fourth kit plus a ball collet (the ball rod being separately packaged since it may come in different sizes); a sixth kit may comprise all the items in the fifth kit plus a ball rod (different kits coming with different size ball rods); a seventh kit may comprise just a ball collet and ball rod (different kits coming with different size ball rod, the user also requiring the fourth kit), and so forth.

Figure 6A:
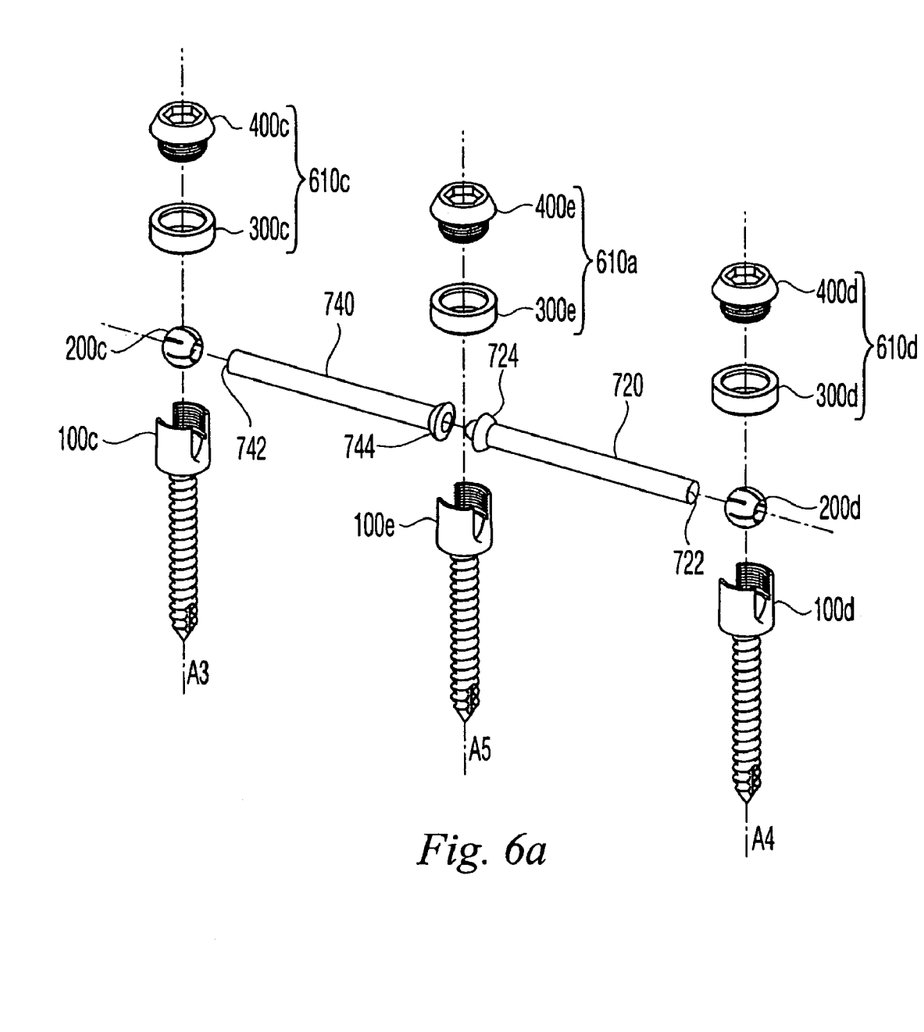
FIG. 6a shows an exploded view of a three-piece assembly in accordance with the present invention.

FIG. 6a shows an exploded view of three-screw assembly 600 in accordance with the present invention. First pedicle screw 100c has associated therewith a longitudinal axis A3, ball collet 200c and cap 610c comprising crown 300c and clamping screw 400c, all as previously described. Second pedicle screw 100d has associated therewith a longitudinal axis A4, ball collet 200d and cap 610d comprising crown 300d and clamping screw 400d. Third pedicle screw 100e has associated therewith a longitudinal axis A3 and cap 610e comprising crown 300e and clamping screw 400e. In the assembly, a male rod member 720 is configured to connect first pedicle screw 100c to third pedicle screw 100e, while a female rod member 740 is configured to connect second pedicle screw 100d to third pedicle screw 100e. Male 728 and female 748 portions of the respective male and female rod members mate within the channel 108 of the third pedicle screw 100e and cooperate to form a ball joint. The shafts of the male and female rod members each separately and independently define a conical region in which each may lay.

Figure 6B:
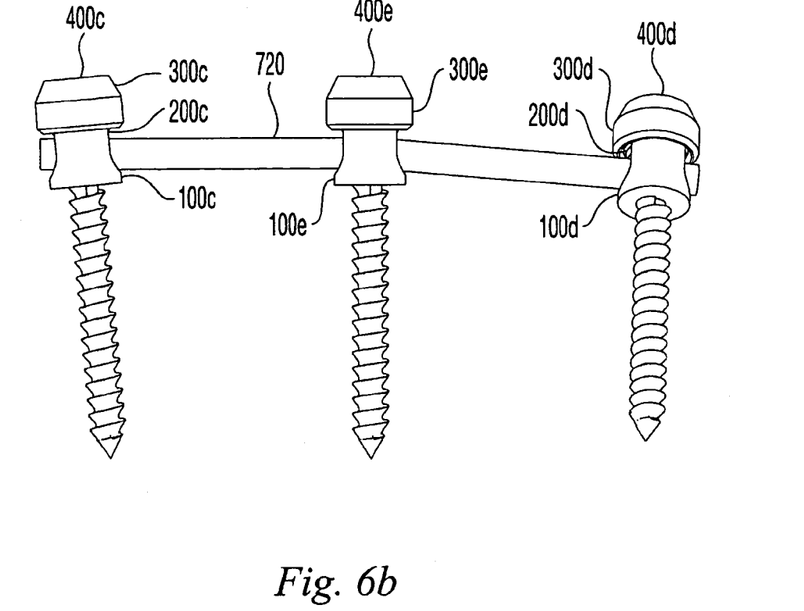
FIGS. 6b and 6c show an assembled three-piece assembly, in a side view and top view, respectively, centered about the middle screw.
Figure 6C:
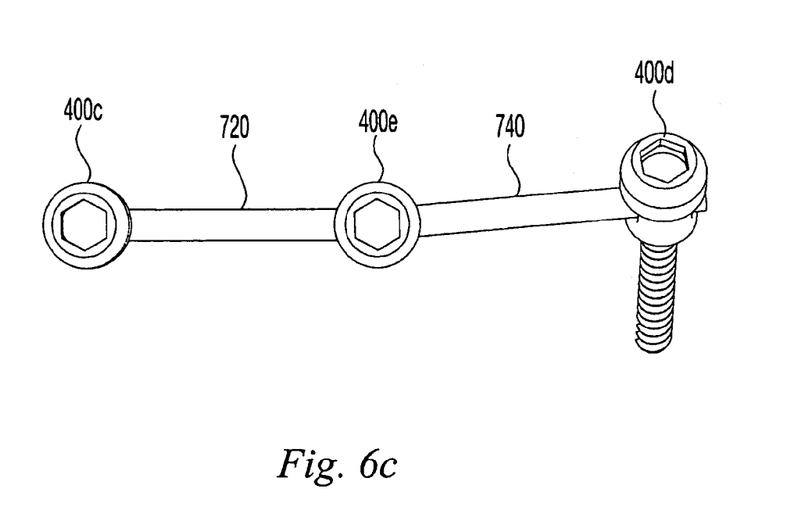

As seen in FIGS. 6b & 6c, when the three-screw assembly 600 is in the assembled state, there is no requirement that the pedicle screws 100c, 100d, 100e be at the same vertical position relative to one another, or, for that matter, be oriented such that their longitudinal axes A3, A4 and A5 are perfectly parallel to one another. This is made possible by the free play afforded the shafts 726, 746 by virtue of the ball joint. This feature allows one-piece pedicle screws in which the insertion portion and the yoke portion are formed with unitary construction, to be used in two-level surgery (i.e., two discs).

In practice, two sets of three pedicle screws, one set on each side of the vertebral column, may be used to provide for a three-level surgery. In such case, on a given side, the three pedicle screws are first inserted into the vertebrae, with the gaps 118 more or less facing in the same direction. Again, male and female rods of varying lengths are provided and during surgery, male and female rods of differing lengths are made available, a rod of an appropriate length perhaps being selected during the surgery itself. It is further understood that the various components are packaged, sold or otherwise made available as kits since they are to be used together. Thus, a first second kit may include three pedicle screws, three caps, and two ball collets, while a second kit may have a male rod member and a female rod member, and these may come in different lengths. Other kit combinations are also possible.

Assembly of the three-screw assembly is next described.

The male 720 and female 740 rod members are brought into abutment with one another and positioned in the channel 108 of the third pedicle screw 100e. The cap may, at this stage, be not fully screw-coupled to the posts of third pedicle screw 100e, thereby resulting in an assembly comprising a pedicle screw 100e, portions of male 720 and female 740 rod members occupying a channel of the pedicle screw 100e and a cap 610e. Next, the ball collets 200c, 200d are mounted onto the shafts 726, 746, respectively and introduced into the channels of the pedicle screws 100c, 100d, respectively. Finally, the caps 610c, 610d & 610e are inserted and tightened.

It is understood that, like the embodiment with the two screw assembly, one may assemble the components in a different order, yet arrive at the same final assembly 600. For instance, the collets 200c, 200d may be mounted onto the shafts 726, 746 before inserting portions of the male 720 and female 740 rod members into the channel of the third pedicle screw 100e. Alternatively, the collets 200c, 200d may first be placed in the channels of pedicle screws 100c, 100d, the first ends 722, 742 of the male 720 and female 740 rod members then inserted into bores 204 of the corresponding collets, and only then having portions of the male 720 and female 740 rod members inserted into the channel of the third pedicle screw 100e. Other variations of these are also possible.

Figure 7A:
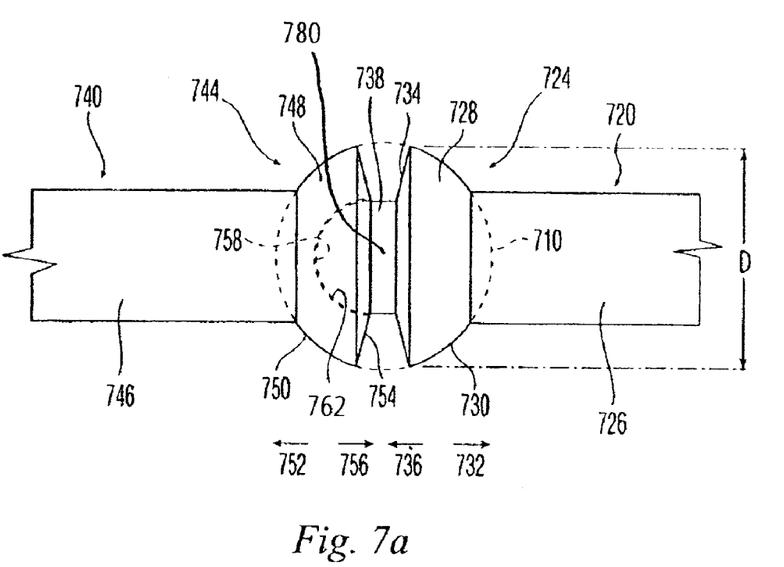
FIG. 7a shows the male and female rod members in accordance with the present invention.
Figure 7B:
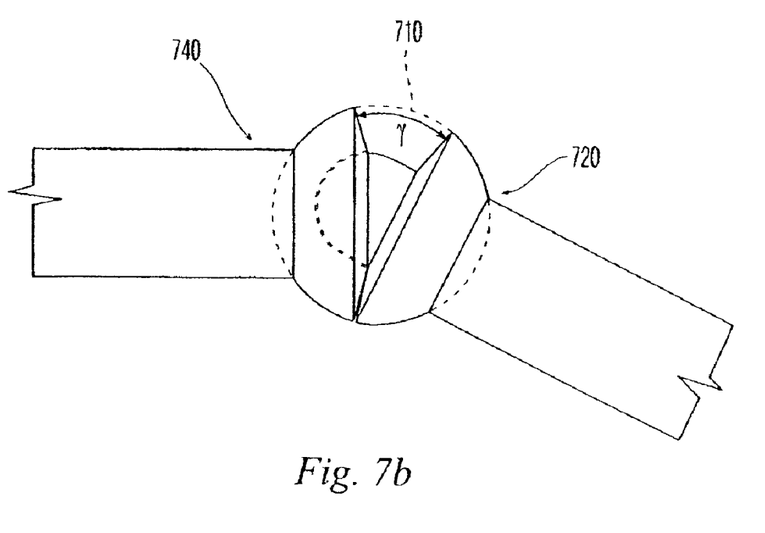
FIG. 7b shows the mated male and female rod members arranged at an angle to one another.

FIGS. 7a and 7b show the construction of the male 720 and female 740 rod members. The male rod member has a first rod end 722, a second rod end 724 and a shaft 726 therebetween. The second rod end 724 comprises a male partial hemispherical ball member 728 having a first convex surface 730 facing an inboard side 732 of the second rod end, and a first conical surface 734 facing the outboard side 736 of the second end, the inboard and outboard sides being indicated by arrows 732, 736, respectively. The conical surface 734 tapers to a shaft 780 of a centrally located male protrusion 738 having a rounded end.

The female rod member has a first rod end 742, a second rod end 744 and a shaft 746 therebetween. The second rod end 744 comprises a female partial hemispherical ball member 748 having a second convex surface 750 facing an inboard side 752 of the second rod end, and a second conical surface 754 facing the outboard side 756 of the second end, the inboard and outboard sides being indicated by arrows 752, 756, respectively. The conical surface 754 tapers to the rim of a centrally located female recess 758 formed in the female partial hemispherical ball member 748.

As seen in FIG. 7a, when the male protrusion 738 enters and abuts the female recess, the first convex surface 730 of the male rod member 720 and the second convex surface of the female rod member lay on the contour of an imaginary sphere 710 having a diameter D, similar to the outer diameter of the ball collet 204 or the bulbous second end 524 of the ball rod 520. Furthermore, the center of the sphere 710 coincides with the center of a hemispherical portion 762 of the male protrusion 738, the convex outer surface of the hemispherical portion 762 being configured to engage the recess 758.

As seen in the two-dimensional view of FIG. 7a, the male rod member 720 has a conical surface that is cut back from the vertical plane by an angle that is preferably between 10°-20°, more preferably between 13°-17° and most preferably about 15°. Similarly, the female rod member 740 has a conical face that is cut back by an angle that is preferably between 10°-20°, more preferably between 13°-17° and most preferably about 15°.

As the male protrusion 738 rotates within the recess 758, the center of the sphere 710 continues to coincide with the center of the hemispherical portion of the male protrusion 738. Thus, so long as the male protrusion 738 is mated to the female recess 758, the convex surfaces 730, 750 remain on the contour of the imaginary sphere, as depicted in FIG. 7b. By virtue of this, the three-piece assembly 600 can accommodate turns of up to about $\gamma=30°$ from collinear, as seen from the top view, along the longitudinal axis A5 of pedicle screw 100e, of FIG. 6c.

Figure 8:
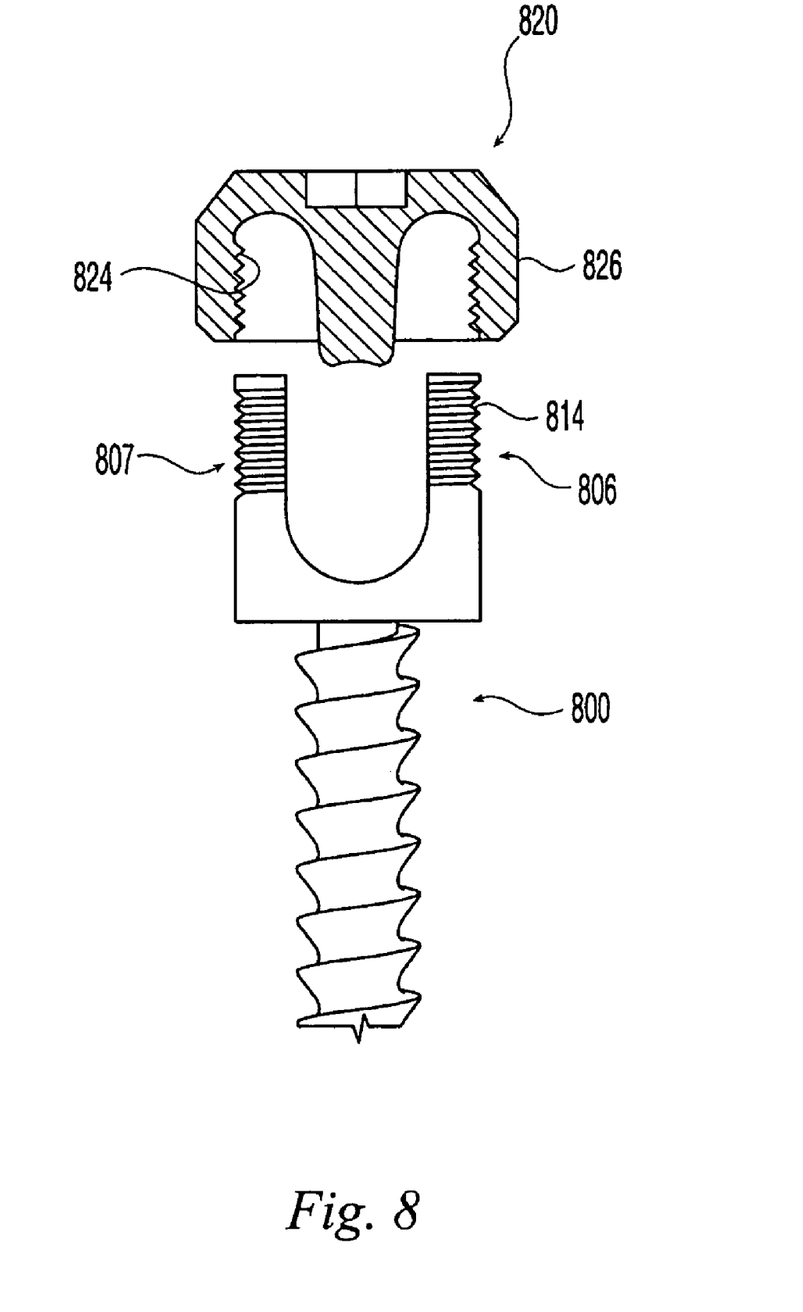
FIG. 8 shows an alternate embodiment of a pedicle screw and cap in accordance with the present invention.

In the foregoing discussion, a two-piece cap comprising a crown 300 and a clamping screw 400 was employed in conjunction with a pedicle screw having posts 106a, 106b provided with radially inwardly facing threads 114. As an alternative, one may instead use a one-piece cap 820 in conjunction with a second embodiment of a pedicle screw 800 having posts 806, 807 with radially outwardly facing threads 814. The one-piece cap 820 has radially inwardly facing threads 824 formed on an inner surface of its skirt 826, the radially inwardly facing threads configured to mate with the radially outwardly facing threads 814 of the pedicle screw 800.

While the foregoing invention was described with respect to certain specific embodiments, it will be appreciated that modifications and variations of the present invention are covered by the above teachings and within the purview of the appended claims without departing from the spirit and intended scope of the invention.

What is claimed is:

1. A pedicle screw assembly comprising:
   a pedicle screw having a pair of spaced-apart threaded posts extending along a longitudinal axis thereof and defining a channel therebetween;
   a ball collet comprising a generally spherical body having a ball collet bore formed therethrough, the ball collet being insertable along the longitudinal axis and into the channel;
   a rod having first and second ends, the first end of the rod being insertable into said ball collet bore; and
   a threaded cap configured and dimensioned to mate with the threaded posts,
   wherein the assembly is adjustable between a disassembled state in which the pedicle screw, ball collet, rod and cap are not secured to one another, and an assembled state in which:
   the ball collet is seated in the channel;
   the rod is gripped by an inner surface of the ball collet bore; and
   the cap is screw-coupled to the post;
   wherein said pedicle screw comprises a threaded insertion portion and yoke portion, and said yoke portion comprises said threaded posts;
   wherein said threaded posts are fixed relative to said threaded insertion portion in said disassembled state;
   wherein the second end of the rod is provided with a partial hemispherical ball member having a convex surface facing an inboard side of the second end;
   wherein the second end of the rod is provided with a conical surface facing an outboard side of the second end; and
   wherein the partial hemispherical ball member has a centrally located protrusion having a spherical portion facing an outboard side of the second end and the conical surface tapers to a shaft of the centrally located protrusion.

2. The assembly according to claim 1, wherein the threaded cap comprises:
   a crown having a cylindrical skirt and a radially inwardly projecting flange; and
   a clamping screw having a threaded portion configured and dimensioned to pass through said flange.

3. The assembly according to claim 2, wherein, when the assembly is in the assembled state:

the cylindrical skirt encircles upper portions of the threaded posts; and the radially inwardly projecting flange overlays axially directed end surfaces of the posts.

4. The assembly according to claim 1, wherein the threaded cap has a concave lower contacting surface with a spherical contour, the concave lower contacting surface abutting the ball collet, when the assembly is in the assembled state.

5. The assembly according to claim 1, wherein the pedicle screw is provided with a concave seat having a spherical contour.

6. The assembly according to claim 1, wherein the posts of the pedicle screw are provided with threads on inner surfaces thereof.

7. The assembly according to claim 1, wherein the ball collet is provided with a plurality of slots spaced about a periphery thereof, each slot connecting an outer surface of the ball collet with the ball collet bore.

8. The assembly according to claim 7, wherein each slot extends in an axial direction along a body axis of the ball collet.

9. The assembly according to claim 1, wherein the second end of the rod is provided with a spherical ball member.

10. The assembly according to claim 9, wherein a diameter of the spherical ball member is similar to a diameter of the ball collet.

11. The assembly according to claim 1, wherein the convex surface of the partial hemispherical ball member follows a spherical contour belonging to a sphere having a diameter similar to a diameter of the ball collet.

12. The assembly according to claim 1, wherein a ratio of a bore diameter of the ball collet to an outer diameter of the ball collet is about 0.6.

13. The assembly according to claim 12, wherein the bore diameter of the ball collet is about 0.2165 inches.

14. The assembly according to claim 12, wherein the spherical body of the ball collet has the outer diameter of about 0.375 inches.

15. A pedicle screw assembly comprising:
first and second pedicle screws, each pedicle screw having a longitudinal axis and a pair of spaced-apart mating posts extending therealong, each pair of mating posts defining a channel therebetween;
a ball collet comprising a generally spherical body having a ball collet bore formed therethrough, the ball collet being insertable into the channel of the first pedicle screw along the first pedicle screw's longitudinal axis;
a rod having a first end and a bulbous second end, the first end of the rod being insertable into said ball collet bore, and the bulbous second end being insertable into the channel of the second pedicle screw along the second pedicle screw's longitudinal axis; and
first and second caps configured and dimensioned to mate with the mating posts of respective first and second pedicle screws,
wherein the assembly is adjustable between a disassembled state in which the first and second pedicle screws, ball collet, rod and caps not secured to one another, and an assembled state in which:
the ball collet is seated in the channel of the first pedicle screw;
the rod is gripped by an inner surface of the ball collet bore;
the bulbous second end of the rod occupies the channel of the second pedicle screw; and
the first and second caps are coupled to the mating posts of respective first and second pedicle screws;

wherein each pedicle screw comprises an integral threaded insertion portion and yoke portion, and said yoke portion comprises said mating posts;

wherein said mating posts are fixed relative to said threaded insertion portion in said disassembled state;

wherein the second end of the rod is provided with a partial hemispherical ball member having a convex surface facing an inboard side of the second end;

wherein the second end of the rod is provided with a conical surface facing an outboard side of the second end; and wherein the partial hemispherical ball member has a centrally located protrusion having a spherical portion facing an outboard side of the second end and the conical surface tapers to a shaft of the centrally located protrusion.

16. The pedicle screw assembly according to claim 15, wherein the bulbous second end comprises a spherical ball member.

17. The pedicle screw assembly according to claim 15, wherein a diameter of the spherical ball member is similar to a diameter of the ball collet.

18. The pedicle screw assembly according to claim 15, wherein said mating posts are threaded posts and said caps are threaded caps.

19. A pedicle screw assembly comprising:
first, second and third pedicle screws, each pedicle screw having a longitudinal axis and a pair of spaced-apart mating posts extending therealong, each pair of mating posts defining a channel therebetween;
first and second ball collets, each comprising a generally spherical body having a ball collet bore formed therethrough, the ball collets being insertable into the channels of respective first and second pedicle screws along corresponding longitudinal axes;
a first rod having a first end insertable into the ball collet bore of the first ball collet, and a first rod second end provided with a first partial hemispherical ball member, the first partial hemispherical ball member having a convex surface facing an inboard side of the first rod second end, and a centrally located protrusion having a spherical portion facing an outboard side of the first rod second end, wherein the first rod second end is provided with a conical surface facing an outboard side of the first rod second end; and wherein the conical surface tapers to a shaft of the centrally located protrusion;
a second rod having a first end insertable into the ball collet bore of the second ball collet, and a second rod second end provided with a second partial hemispherical ball member, the second partial hemispherical ball member having a convex surface facing an inboard side of the second rod second end, and a centrally located recess facing an outboard side of the second rod second end; and
first, second and third caps configured and dimensioned to mate with the mating posts of respective first, second and third pedicle screws,
wherein the assembly is adjustable between a disassembled state in which the pedicle screws, ball collets, rods and caps are not secured to one another, and an assembled state in which:
the first and second ball collets occupy channels of the first and second pedicle screws, respectively;
the first rod is gripped by an inner surface of the first ball collet bore and the second rod is gripped by an inner surface of the second ball collet bore;

the first and second partial hemispherical ball members oppose one another within the channel of the third pedicle screw, with the protrusion at least partially entering the recess; and the three caps are coupled to the pairs of mating posts of three pedicle screws;

wherein each pedicle screw comprises a threaded insertion portion and yoke portion, and said yoke portion comprises said mating posts;

wherein said mating posts are fixed relative to said threaded insertion portion in said disassembled state; and wherein when the spherical portion of the centrally located protrusion has at least partially entered the recess, a joint is established in which a range of motion between the first rod and second rod is achieved without rotation of either rod about a longitudinal axis of the protrusion.

20. The pedicle screw assembly according to claim 19, wherein the convex surfaces of the first and second partial hemispherical ball members opposing one another within the channel of the third pedicle screw together follow a spherical contour belonging to a sphere having a diameter similar to a diameter of either ball collet.

21. The pedicle screw assembly according to claim 19, wherein:
the first rod second end is provided with a first conical surface facing an outboard side thereof; and
the second rod second end is provided with a second conical surface facing an outboard side thereof.

22. The pedicle screw assembly according to claim 21, wherein when the centrally located protrusion has at least partially entered the recess, the first rod can accommodate turns of up to about 40 degrees from collinear with respect to the second rod.

23. The pedicle screw assembly according to claim 22, wherein the spherical body of the ball collet has an outer diameter of about 0.375 inches.

24. The pedicle screw assembly according to claim 21, wherein the first conical surface and the second conical surface are cut back from the vertical plane by an angle that is preferably in a range of 10 to 20 degrees.

25. The pedicle screw assembly according to claim 19, wherein the threaded insertion portion and yolk of the pedicle screw is an integral threaded insertion portion and yolk.

26. The pedicle screw assembly according to claim 19, wherein said mating posts are threaded posts and said caps are threaded caps.

27. A pedicle screw assembly comprising:
a pedicle screw having a pair of spaced-apart mating posts extending along a longitudinal axis thereof and defining a channel therebetween;
a first rod having a first rod end provided with a first partial hemispherical ball member, the first partial hemispherical ball member having a convex surface facing an inboard side of the first rod end; and
a second rod having second rod end provided with a second partial hemispherical ball member, the second partial hemispherical ball member having a convex surface facing an inboard side of the second rod end, and a centrally located recess facing an outboard side of the second rod end; and
a cap configured and dimensioned to mate with the pair of spaced-apart mating posts,
wherein the assembly is adjustable between a disassembled state in which the pedicle screw, first and second rods and cap are not secured to one another, and an assembled state in which:
the first and second partial hemispherical ball members oppose one another within the channel of the pedicle screw, with the protrusion at least partially entering the recess; and
the cap coupled to the pair of threaded posts;
wherein said pedicle screw comprises an integral threaded insertion portion and yoke portion, and said yoke portion comprises said threaded posts;
wherein said mating posts are fixed relative to said threaded insertion portion in said disassembled state; and
wherein:
the first partial hemispherical ball member of the first rod end is provided with a first conical surface facing the outboard side of the first rod end and wherein the first partial hemispherical ball member of the first rod end has a centrally located protrusion having a spherical portion facing an outboard side of the first rod end and the conical surface tapers to a shaft of the centrally located protrusion; and
the second rod end is provided with a second conical surface facing the outboard side of the first rod end and the second conical surface tapers to the centrally located recess.

28. The pedicle screw assembly according to claim 27, wherein the first conical surface and the second conical surface are each cut back from the vertical plane by an angle that ranges from 10 to 20 degrees and when the centrally located protrusion has at least partially entered the recess, a joint is established in which a range of motion between the first rod and second rod may be achieved without rotation of either rod about a longitudinal axis of the centrally located protrusion.

29. The pedicle screw assembly according to claim 28, wherein when the centrally located protrusion has at least partially entered the recess, the first rod accommodates turns of up to 40 degrees from collinear with respect to the second rod.

30. The pedicle screw assembly according to claim 27, wherein said mating posts are threaded posts and said caps are threaded caps.

* * * * *